United States Patent [19]

Nakao et al.

[11] Patent Number: 5,360,412
[45] Date of Patent: Nov. 1, 1994

[54] METHOD AND DEVICE FOR REGULATING INTRAVENOUS FLOW

[76] Inventors: Naomi L. Nakao, 303 E. 57th St., New York, N.Y. 10022; John V. Mizzi, 30 Cramer Rd., RFD #3, Poughkeepsie, N.Y. 12603

[21] Appl. No.: 956,113

[22] Filed: Oct. 5, 1992

[51] Int. Cl.⁵ ............................................. A61M 5/00
[52] U.S. Cl. ................................. 604/247; 604/251; 137/395; 137/403; 137/504
[58] Field of Search ............ 604/52, 246, 247, 249, 604/251-255, 407; 137/395, 400, 401, 403, 404, 498, 501, 504

[56] References Cited
U.S. PATENT DOCUMENTS

| | | | |
|---|---|---|---|
| 2,668,555 | 2/1954 | Bartolat | 137/498 |
| 2,704,552 | 3/1955 | De Verteuil | 137/498 |
| 3,938,539 | 2/1976 | Strouth et al. | 604/246 |
| 4,043,332 | 8/1977 | Metcalf | 137/501 |
| 4,096,879 | 6/1978 | Serur et al. | 604/246 |
| 4,268,222 | 5/1981 | Palti | 604/254 |
| 4,328,820 | 5/1982 | Serur | 604/254 |

FOREIGN PATENT DOCUMENTS 2282278 3/1976 France .................... 604/254

*Primary Examiner*—John D. Yasko
*Assistant Examiner*—Anthony Gutowski
*Attorney, Agent, or Firm*—R. Neil Sudol; Henry D. Coleman

[57] ABSTRACT

A device for controlling flow rate in an intravenous line comprises a housing having an inlet port adapted to be connected to an incoming segment of an intravenous line and an outlet port adapted to be connected to an outgoing segment of the intravenous line. A valve is disposed in the housing between the inlet port and the outlet port. The device further comprises a first valve adjustment mechanism mounted to the housing and operatively connected to the valve for setting the valve to select a desired flow rate, the first valve adjustment mechanism being manually adjustable for selecting the desired flow rate. A second valve adjustment mechanism is mounted to the housing and is operatively connected to the valve for automatically and temporarily closing the valve in response to the exceeding of the desired flow rate by an average flow rate of intravenous fluid into the housing through the inlet port.

23 Claims, 1 Drawing Sheet

METHOD AND DEVICE FOR REGULATING INTRAVENOUS FLOW

BACKGROUND OF THE INVENTION

This invention relates to an intravenous fluid supply system. More particularly, this invention relates to a device for regulating the rate of fluid flow through an intravenous line into a patient. This invention also relates to an associated method for controlling the rate of intravenous feeding.

In hospitals, intravenous infusion rates are stipulated by doctors' prescriptions which are usually specified in terms of cubic centimeters per hour. Such a prescription is usually converted by a nurse or other hospital personnel into a number of drops of intravenous fluid per minute. The drops are measured by monitoring a so-called "drip chamber" wherein drops fall from an inlet through an air space into a reservoir of fluid at the bottom of the drip chamber. Fluid then flows out through an outlet port at the bottom of the reservoir into an intravenous line extending to a patient. Depending on the model of drip chamber, a uniform size drop is produced, enabling conversion of cubic centimeters per hour into drops per minute. The number of drops per minute is controlled by adjusting a roller valve downstream of the drip chamber.

It would be desirable to dispense with the units conversion and the time consuming flow regulation procedure by providing a valve with a simple setting in terms of cubic centimeters per hour.

An intravenous system is a pressure driven system wherein pressure from an elevated bag or reservoir is fed through a drip chamber, sometimes a check valve, a regulating clamp, various hose fittings, and finally a cannula or catheter at the patient. All of these elements provide pressure loss, and it is the balancing of all these via the pressure loss in the regulating valve against the pressure from the bag that regulates flow.

In designing a system which is accurate and responsive, it is important to note that two factors vary from infusion to infusion. One factor is orifice size of the catheter or cannula. A pediatric version, for example, is smaller than adult sizes. Another factor is venous back pressure which varies somewhat from patient to patient. Occasionally, even the initial pressure source can be a variable if the height varies at which the bag is suspended. Viscosity of the intravenous fluid may also be a variable. In addition, pressure affecting factors can change even during infusion. The pressure provided by the bag decreases slightly as the level falls. A patient's venous back pressure can vary. The condition of the infusion site can change, resulting in a pressure loss. For these reasons, infusion rate is routinely checked and adjusted periodically by a nurse during an infusion.

OBJECTS OF THE INVENTION

An object of the present invention is to provide an improved method for regulating an intravenous flow rate.

Another object of the present invention is to provide such a method which results in increased accuracy.

Another, more particular, object of the present invention is to provide such a method which is easy and quick to implement.

An associated object of the present invention is to provide a device connectable in an intravenous flow line for facilitating the setting of flow rate.

Yet another object of the present invention is to provide an intravenous flow rate regulator which is inexpensive to manufacture.

A further object of the present invention is to provide an intravenous flow rate regulator which functions as a servo valve with feedback.

Yet another object of the present invention is to provide a flow regulating valve which uses a simple mechanical technique to achieve a relatively high precision in regulating flow rate.

These and other objects of the present invention will be apparent from the drawings and detailed descriptions herein.

SUMMARY OF THE INVENTION

A device for controlling flow rate in an intravenous line comprises, in accordance with one conceptualization of the present invention, a housing having an inlet port adapted to be connected to an incoming segment of an intravenous line and an outlet port adapted to be connected to an outgoing segment of the intravenous line. A valve is disposed in the housing between the inlet port and the outlet port. The device further comprises a first valve adjustment mechanism mounted to the housing and operatively connected to the valve for setting the valve to select a desired flow rate, the first valve adjustment mechanism being manually adjustable for selecting the desired flow rate. A second valve adjustment mechanism is mounted to the housing and is operatively connected to the valve for automatically and temporarily closing the valve in response to the exceeding of the desired flow rate by an average flow rate of intravenous fluid into the housing through the inlet port.

According to further features of the present invention, the housing includes a pair of housing parts movably mounted to one another, while the valve includes a valve seat mounted to one of the housing parts and a valve member mounted to the other of the housing parts. The first valve adjustment mechanism then includes means such as a camming assembly connected to the housing for moving the housing parts relative to one another. The camming assembly may include a pair of pins rigid with one of the housing parts and a pair of camming slots on yet another housing part.

According to another feature of the present invention, the flow regulating device further comprises a bellows-like element connecting the first two housing parts to one another. The bellows-like element enables the housing parts to move relative to one another while maintaining a fluid seal preventing intravenous fluid from escaping the housing except through the outlet port.

According to an additional feature of the present invention, the second valve adjustment mechanism includes an accumulator movably mounted to the housing and rigidly connected to a valve member of the valve for moving the valve member in response to accumulated weight of intravenous fluid received via the input port. The accumulator is provided with an outflow aperture for emptying the accumulator of collected intravenous fluid. The outflowing fluid collects in a reservoir located below the accumulator and at the output port of the device.

According to yet another feature of the present invention, the accumulator is mounted to the housing via a spring.

The second valve adjustment mechanism preferably includes means operatively connected to the valve for closing the valve in response to increased weight of accumulated intravenous fluid received into the housing via the inlet port.

A device for use in an intravenous assembly comprises, in accordance with another conceptualization of the present invention, a housing with an inlet port and an outlet port, first components on the housing for defining a primary drip chamber upstream of the outlet port, a valve member and a valve seat in the housing at a lower end of the primary drip chamber and upstream of the outlet port, and second components in the housing for defining a secondary drip chamber upstream of the primary drip chamber and downstream of the inlet port. The second housing components are provided with at least one outflow aperture for enabling flow of collected intravenous fluid from the secondary drip chamber to the primary drip chamber. The valve member is rigid with housing components defining the secondary drip chamber, while elements are provided for movably mounting the second housing components to the housing so that a distance of the valve member from the valve seat varies in accordance with an amount of intravenous fluid accumulated in the secondary drip chamber.

A device for use in an intravenous assembly comprises, in accordance with a relatively detailed conceptualization of the present invention, a housing with an inlet port and an outlet port, and an accumulator movably mounted to the housing for receiving intravenous drops from the inlet port. The accumulator is provided with an outflow aperture for emptying the accumulator of collected intravenous fluid. A valve member is rigid with the accumulator and spaced from the accumulator on a downstream side thereof, while a valve seat is movably mounted to at least a portion of the housing and is disposed downstream of the accumulator and upstream of the outlet port in the housing. The valve member is aligned with the valve seat to cooperate therewith to form a servo valve. Valve adjustment components are provided on the housing for adjusting the position of the valve seat relative to the housing, whereby a desired flow rate through the device can be manually established. Support components are provided for supporting the accumulator on the housing so that instantaneous distance of the valve member from the valve seat is variable essentially in accordance with an amount of intravenous fluid held in the accumulator.

In accordance with another feature of the present invention, the housing includes a main body member and an auxiliary portion movably attached to the main body member, the valve seat being disposed in the auxiliary portion. The adjustment componentry includes means operatively connected to the auxiliary portion of the housing for changing the position thereof relative to the main body member.

The adjustment components may include a camming mechanism operatively connected to the main body member and the auxiliary housing portion. The camming mechanism may specifically include a pair of pins rigid with one of the main body member and a pair of camming slots on yet another housing member, the pins at least partially traversing respective ones of the slots.

The auxiliary portion may be a panel connected to the main body member by a bellows-like portion of the housing. The support components include a spring engaging the housing and the accumulator. The spring may take the specific form of a helical compression spring.

In accordance with another feature of the present invention, the device further comprises indicator marks or signs on the housing for providing a scale to identify different intravenous flow rates.

In accordance with yet another feature of the present invention, the device also comprises damping elements rigid with the valve member for providing a damping force to slow dithering of the valve member during operation.

A method for regulating flow of intravenous fluid in an intravenous line comprising, in accordance with the present invention, the steps of (a) setting a desired flow rate through the intravenous line, (b) accumulating intravenous fluid in a first reservoir, (c) leaking intravenous fluid from the first reservoir into a second reservoir, and (d) temporarily blocking fluid from escaping the second reservoir if the amount of fluid in the first reservoir is greater than an amount determined by the set desired flow rate.

Pursuant to another feature of the present invention, setting the desired flow rate is accomplished by moving a valve seat relative to a cooperating valve member. This movement of the valve member relative to the valve seat may be implemented by rotating a first housing part relative to a second housing part and simultaneously changing an axial relationship of the first housing part and the second housing part via a camming action, the valve member and the valve seat being movably connected to one housing part for independent motion relative thereto.

Pursuant to another feature of the present invention, the temporary blocking of the fluid is achieved by moving the valve member and the valve seat towards one another in response to an increased weight of accumulated intravenous fluid in the first reservoir. The step of temporarily blocking may additionally include the step of moving the first reservoir relative to a housing in a predetermined direction. In that event, the method further comprises the step of pushing the first reservoir in another direction opposite to the predetermined direction upon a temporary closure of the valve member and the valve seat.

A method for regulating an intravenous flow rate in accordance with the present invention results in increased accuracy. A servo valve with feedback essentially tracks changes in pressure and continuously changes flow rate in accordance with a selected flow rate and in response to changing flow and/or pressure conditions.

A flow regulator device in accordance with the present invention is easy and quick to set. The device is simply connected to intravenous flow tubes and the housing parts rotated with respect to one another to select a desired flow rate.

A flow regulating valve uses a simple mechanical technique to achieve a relatively high precision in regulating flow rate.

DETAILED DESCRIPTION

Figure 1:
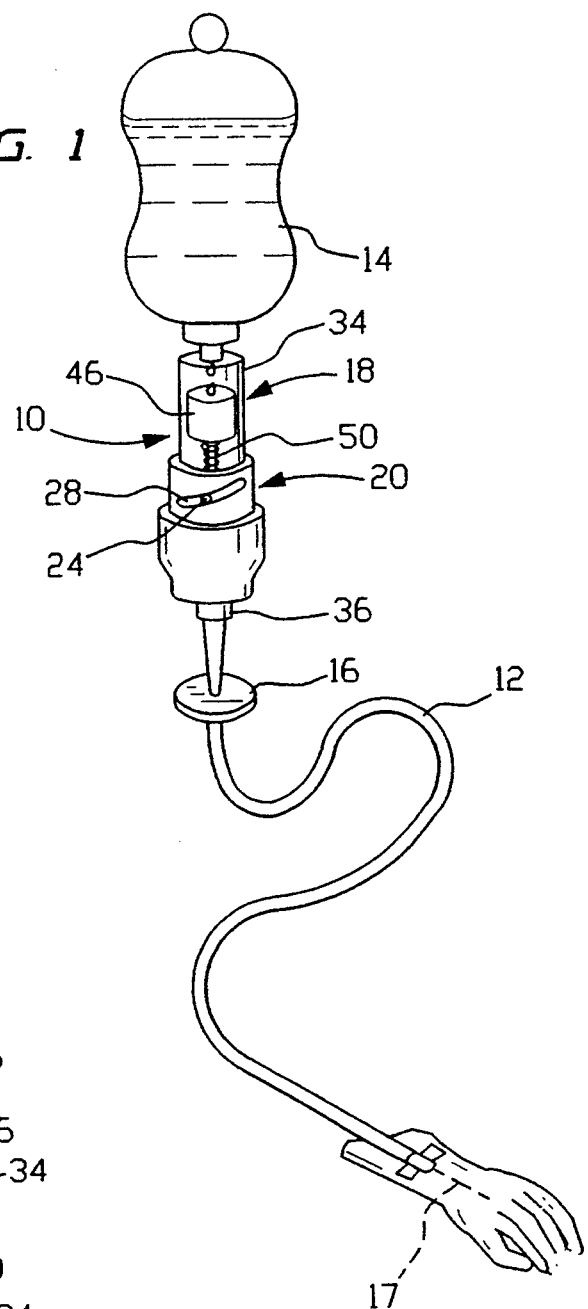
FIG. 1 is a schematic perspective view of an intravenous feed assembly, showing a flow regulating device in accordance with the present invention.

As illustrated in FIG. 1, a servo-valve flow regulating device 10 is inserted in an intravenous line 12 between an intravenous fluid source 14 and an optional check valve 16. A lower end of intravenous line 12 is connected to a catheter or cannula 17 which is inserted into a patient's vein.

Figure 2:
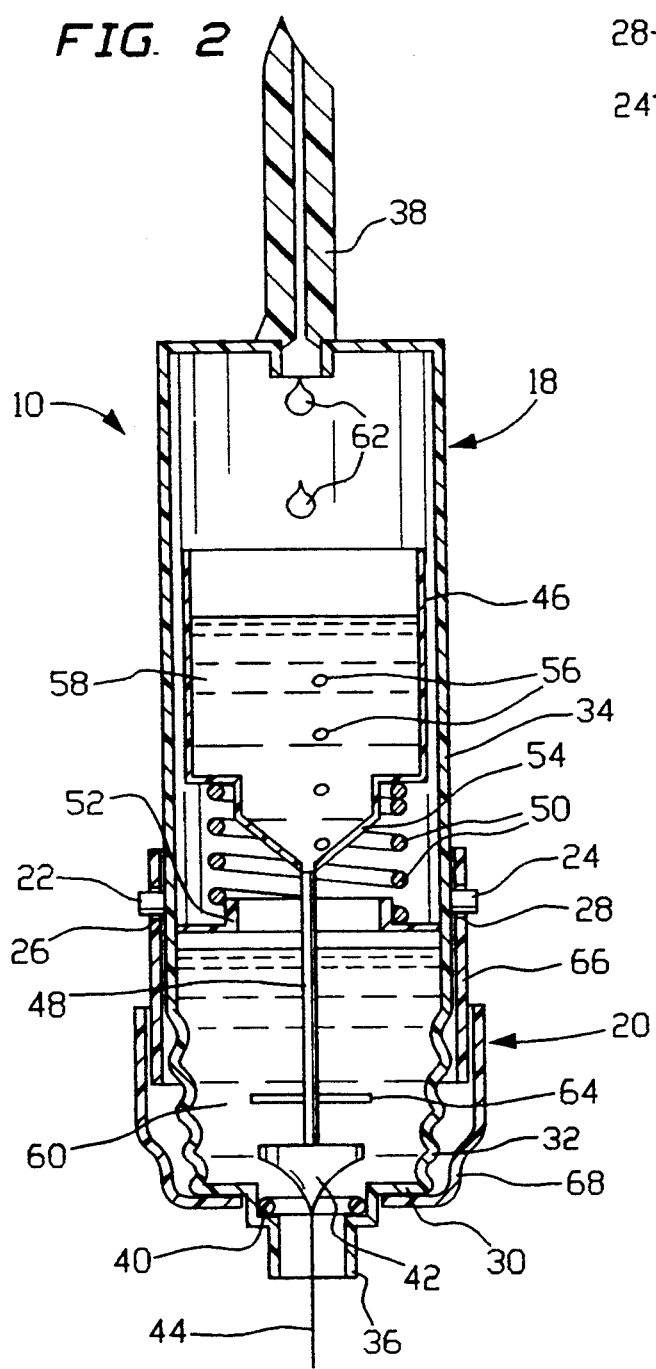
FIG. 2 is a schematic cross-sectional view of the flow regulating device of FIG. 1.

As shown in FIGS. 1 and 2, flow regulating device 10 includes an upper housing part 18, which is generally fixed with respect to intravenous source 14, and a lower housing part or setting collar 20 which is rotatably secured to upper housing part 18 via a pair of camming pins 22 and 24. Pins 22 and 24 are fixed to upper housing part 18, while lower housing part 20 is provided with a pair of arcuate camming slots 26 and 28 traversed by respective pins 22 and 24.

Upper housing part 18 has an auxiliary lower portion in the form of a ring panel 30 which is connected via an integral bellows-like housing portion 32 to a main body member 34 of upper housing part 18. Bellows-like portion 32 enables relative motion between ring 30 and main body member 34 while maintaining a fluid seal preventing intravenous fluid from escaping the housing except through an outlet port 36 attached to ring 30. Outlet port 36 is adapted to be connected to a lower segment of intravenous line 12 (FIG. 1). Upper housing part 18 is provided on main body member 34 with a piercing spike 38 which forms an inlet port and enables attachment of housing part 18 to an upper segment of intravenous line 12 extending from intravenous fluid source 14.

At outlet port 36, essentially on an upstream side thereof, ring 30 carries a valve seat 40 which is vertically or longitudinally aligned with and cooperates with a valve member 42. Valve member 42 is provided on an outlet or downstream side with an axially extending guide wire and calibration nib 44 and is connected on an inlet or upstream side to an accumulator cup 46 via a rod or valve stem 48.

Accumulator cup 46 is mounted to main body member 34 of upper housing part 18 via a helical compression spring 50. Spring 50 may be fixed at an upper or upstream end to accumulator cup 46 via, for example, a force-lock fit. Spring 50 may be similarly attached at a lower or downstream end to a collar 52 integral with main body member 34. At a lower end, accumulator cup 46 is provided with an outflow aperture 54 for emptying the accumulator cup of intravenous fluid which the cup has collected from inlet port 38 during operation of the device. Accumulator cup 46 may be provided with a plurality of additional outflow apertures 56 which serve to extend the operational range of the flow regulating device. Additional outflow apertures 56 are spaced from one another in a vertical array to provide for a greater range of regulatable flow rates.

Flow regulating device 10 incorporates a first mechanism, including camming pins 22 and 24 and slots 26 and 28, for adjusting the distance between valve seat 40 and valve member 42. In order to select a desired flow rate through flow regulating device 10, a user twists or rotates lower housing part 20 relative to upper housing part 18. During the relative rotation of lower housing part 20 and upper housing part 18, pins 22 and 24 ride along slots 26 and 28 and, through a camming action, move lower housing part 20 axially relative to upper housing part 18. This relative axial motion of the two housing parts 18 and 20 forces ring panel 30 to move relative to main body member 34, thereby adjusting the distance of valve seat 40 from valve member 42 to provide a valve opening corresponding to a desired flow rate. Housing parts 18 and 20 are provided along their outer sides with scale markings to indicate cubic centimeters per hour and drops per minute, in accordance with the angular position of lower housing part 20 relative to upper housing part 18. The cubic centimeters per hour scale may be provided along slot 26, while the drops per minute scale may be provided along slot 28.

Flow regulating device 10 additionally incorporates a second valve adjustment mechanism including accumulator cup 46, spring 50 and outflow aperture 54, for automatically and temporarily closing valve member 42 and valve seat 40 in response to the exceeding of the selected desired flow rate by an average flow rate of intravenous fluid into the housing through inlet port 38. Accumulator cup 46 defines a secondary drip chamber or reservoir 58 upstream of a primary drip chamber or reservoir 60 inside bellows-like portion 32 of housing portion 18. Drops of intravenous fluid 62 arriving via inlet port 38 are accumulated in accumulator cup 46. If the rate of incoming drops 62 is too great and accumulator cup 46 fills to an excessive level, the weight of the cup overcomes a biasing force exerted by spring 50 and causes valve member 42 to engage valve seat 40, thereby preventing intravenous fluid from leaving primary drip chamber or reservoir 60 through outlet port 36. A consequent increase in pressure inside housing part 18 stops the flow of incoming drops until the level of intravenous fluid in secondary drip chamber or reservoir 58 falls, thereby reducing the weight of accumulator cup 46 to result in a lifting of valve member 42 from seat 40.

Flow regulating device 10 is optionally provided on valve stem 48 with a plate or ring 64. During operation of the device 10, plate or ring 64 is located in primary drip chamber or reservoir 60. Plate or ring 64 serves to damp the motion of the secondary flow adjustment componentry, namely, accumulator cup 46, valve stem 48 and valve member 42, relative to housing part 18, thereby reducing a dithering of that componentry relative to the housing. Damping plate or ring 64 renders the flow regulating device 10 more stable and less sensitive to external jarring forces.

Flow regulating device 10 continuously monitors flow by comparing it to a desired setpoint and adjusting a restriction (the valve opening between member 42 and seat 40) to facilitate an average flow close to the setpoint. Flow regulating device 10 thus incorporates a form of feedback control based upon a simple mechanical technique.

It is to be noted that the flow regulating device requires no penetrations of the housing which would necessitate moving seals or which would compromise the leak-free integrity of the housing. Setting the desired flow rate is accomplished entirely externally to housing part 18. Since the servo valve actually monitors flow, it can compensate for variations in pressure supply and pressure losses.

A simple on/off clamp or plastic restrictor (not shown) may be provided downstream of flow regulating device 10 in intravenous line 12.

The adjustment of the position of lower housing part 20 relative to upper housing part 18 serves to modify the distance that spring 50 has to compress before valve member 42 meets valve seat 40. The same relative position adjustment determines the maximum weight of intravenous fluid held in reservoir 58 defined by accumulator cup 46. Concomitantly, the average position of accumulator cup 46 in housing part 18 is preselected by the adjustment of housing parts 18 and 20.

The final step in the manufacturing process is calibration. To facilitate calibration, housing part 20 comprises an upper section 66 and a lower section 68. Guide wire 44 is used as a calibration tool. The length of wire 44 is such that a properly adjusted valve at a certain midscale setting will cause the wire end to be flush with the free end of outlet port or hose coupling 36, with the flow regulating device 10 vertical and empty. Valve member 42 is pressed to this position in a fixture, the end of guide wire 44 being detected at the free end of outlet port 36. Upon attainment of this calibration position, upper section 66 and lower section 68 are adhesively bonded or heat sealed to one another while in the fixture, thereby effectively compensating for slight variations in spring constant, spring free length, and the empty weight of accumulator cup 46, valve stem 48 and valve member 42.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A device for use in an intravenous assembly, comprising:
    a housing with an inlet port and an outlet port;
    accumulator means movably mounted to said housing for receiving intravenous drops from said inlet port, said accumulator means being provided with outflow means for emptying said accumulator means of collected intravenous fluid;
    a valve member rigid with said accumulator means and spaced from said accumulator means on a downstream side thereof;
    a valve seat movably mounted to said housing and disposed downstream of said accumulator means and upstream of said outlet port, said valve member being aligned with said valve seat to cooperate therewith to form a servo valve;
    adjustment means for adjusting the position of said valve seat relative to said housing, whereby a desired flow rate through the device can be manually established;
    support means for supporting said accumulator means on said housing so that instantaneous distance of said valve member from said valve seat is variable essentially in accordance with an amount of intravenous fluid held in said accumulator means; and
    indicator means on said housing for providing a scale to identify different intravenous flow rates.

2. The device defined in claim 1 wherein said housing includes a main body member and an auxiliary portion movably attached to said main body member, said valve seat being disposed in said auxiliary portion, said adjustment means including means operatively connected to said auxiliary portion for changing the position thereof relative to said main body member.

3. The device defined in claim 2 wherein said adjustment means includes a camming mechanism operatively connected to said main body member and said auxiliary portion.

4. The device defined in claim 3 wherein said camming mechanism further includes a pair of pins rigid with said main body member, said camming mechanism further including a pair of camming slots on an ancillary housing element rotatably mounted to said main body member, said pins at least partially traversing respective ones of said slots.

5. The device defined in claim 2 wherein said auxiliary portion is a panel connected to said main body member by a bellows-like portion of said housing.

6. The device defined in claim 1 wherein said support means includes a spring engaging said housing and said accumulator means.

7. The device defined in claim 6 wherein said spring is a helical compression spring.

8. The device defined in claim 1 wherein said outflow means includes a hole in said accumulator means.

9. The device defined in claim 1 wherein said outflow means includes a plurality of holes disposed at different fluid levels in said accumulator means.

10. The device defined in claim 1, further comprising damping means rigid with said valve member for providing a damping force to slow dithering of said valve member during operation.

11. A device for controlling flow rate in an intravenous line, comprising:
    a housing having an inlet port adapted to be connected to an incoming segment of an intravenous line and an outlet port adapted to be connected to an outgoing segment of the intravenous line;
    a valve disposed in said housing between said inlet port and said outlet port;
    first valve adjustment means mounted to said housing and operatively connected to said valve for setting said valve to select a desired flow rate, said first valve adjustment means being manually adjustable for selecting said desired flow rate;
    second valve adjustment means mounted to said housing and operatively connected to said valve for automatically and temporarily closing said valve in response to the exceeding of said desired flow rate by an average flow rate of intravenous fluid into said housing through said inlet port; and
    indicator means on said housing for providing a scale to identify different intravenous flow rates,
    said housing including a pair of housing parts movably mounted to one another, said valve including a valve seat mounted to one of said housing parts and a valve member mounted to the other of said housing parts, said first valve adjustment means including means connected to said housing for moving said housing parts relative to one another.

12. The device defined in claim 11 wherein said means for moving includes a camming assembly mounted to said housing and operatively connected to said valve.

13. The device defined in claim 12 wherein said camming assembly includes a pair of pins rigid with one of said housing parts, said camming assembly further including a pair of camming slots on an ancillary housing part, said pins at least partially traversing respective ones of said slots.

14. The device defined in claim 11, further comprising a bellows-like element connecting said housing parts to one another.

15. The device defined in claim 11 wherein said second valve adjustment means includes means operatively connected to said valve for closing said valve in response to increased weight of accumulated intravenous fluid received into said housing via said inlet port.

16. A device for controlling flow rate in an intravenous line, comprising:
   a housing having an inlet port adapted to be connected to an incoming segment of an intravenous line and an outlet port adapted to be connected to an outgoing segment of the intravenous line;
   a valve disposed in said housing between said inlet port and said outlet port;
   first valve adjustment means mounted to said housing and operatively connected to said valve for setting said valve to select a desired flow rate, said first valve adjustment means being manually adjustable for selecting said desired flow rate;
   second valve adjustment means mounted to said housing and operatively connected to said valve for automatically and temporarily closing said valve in response to the exceeding of said desired flow rate by an average flow rate of intravenous fluid into said housing through said inlet port; and
   indicator means on said housing for providing a scale to identify different intravenous flow rates,
   said second valve adjustment means including accumulator means movably mounted to said housing and rigidly connected to a valve member of said valve for moving said valve member in response to accumulated weight of intravenous fluid received via said input port, said accumulator means being provided with outflow means for emptying said accumulator means of collected intravenous fluid.

17. The device defined in claim 16 wherein said accumulator means is mounted to said housing via a spring.

18. A method for regulating an intravenous flow rate, comprising the steps of:
   setting a desired flow rate through an intravenous line, said step of setting including the step of moving a valve seat relative to a cooperating valve member;
   guiding intravenous fluid into a first reservoir in said intravenous line;
   accumulating intravenous fluid in said first reservoir;
   leaking intravenous fluid from said first reservoir into a second reservoir in said intravenous line;
   temporarily blocking fluid from escaping said second reservoir if the amount of fluid in said first reservoir is greater than an amount determined by the set desired flow rate,
   said step of temporarily blocking including the step of moving said valve member and said valve seat towards one another in response to an increased weight of accumulated intravenous fluid in said first reservoir; and
   guiding fluid from said second reservoir further along said intravenous line to a patient.

19. The method defined in claim 18 wherein said step of moving includes the step of rotating a first housing part relative to a second housing part and simultaneously changing an axial relationship of said first housing part and said second housing part via a camming action, said valve seat and said valve member each being movably connected independently to one of said first housing part and said second housing part.

20. The method defined in claim 18 wherein said step of temporarily blocking additionally includes the step of moving said first reservoir relative to a housing in a predetermined direction.

21. The method defined in claim 18, further comprising the step of pushing said first reservoir in another direction opposite to said predetermined direction upon a temporary closure of said valve member and said valve seat.

22. A device for use in an intravenous assembly, comprising:
   a housing with an inlet port and an outlet port, said housing includes a main body member and an auxiliary portion movably attached to said main body member;
   accumulator means movably mounted to said housing for receiving intravenous drops from said inlet port, said accumulator means being provided with outflow means for emptying said accumulator means of collected intravenous fluid;
   a valve member rigid with said accumulator means and spaced from said accumulator means on a downstream side thereof;
   a valve seat movably mounted to said housing and disposed downstream of said accumulator means and upstream of said outlet port, said valve member being aligned with said valve seat to cooperate therewith to form a servo valve, said valve seat being disposed in said auxiliary portion;
   adjustment means for adjusting the position of said valve seat relative to said housing, whereby a desired flow rate through the device can be manually established, said adjustment means including a camming mechanism operatively connected to said main body member and said auxiliary portion for changing the position of said auxiliary portion relative to said main body member, said camming mechanism including a pair of pins rigid with said main body member and further including a pair of camming slots on an ancillary housing element rotatably mounted to said main body member, said pins at least partially traversing respective ones of said slots; and
   support means for supporting said accumulator means on said housing so that instantaneous distance of said valve member from said valve seat is variable essentially in accordance with an amount of intravenous fluid held in said accumulator means.

23. A device for controlling flow rate in an intravenous line, comprising:
   a housing having an inlet port adapted to be connected to an incoming segment of an intravenous line and an outlet port adapted to be connected to an outgoing segment of the intravenous line, said housing including a pair of housing parts movably mounted to one another;
   a bellows-like element connecting said housing parts to one another;
   a valve disposed in said housing between said inlet port and said outlet port, said valve including a valve seat mounted to one of said housing parts and a valve member mounted to the other of said housing parts;
   first valve adjustment means mounted to said housing and operatively connected to said valve for setting said valve to select a desired flow rate, said first valve adjustment means being manually adjustable for selecting said desired flow rate, said first valve adjustment means including means connected to said housing for moving said housing parts relative to one another; and second valve adjustment means mounted to said housing and operatively connected to said valve for automatically and temporarily closing said valve in response to the exceeding of said desired flow rate by an average flow rate of intravenous fluid into said housing through said inlet port.

* * * * *

UNITED STATES PATENT AND TRADEMARK OFFICE
CERTIFICATE OF CORRECTION

PATENT NO. : 5,360,412
DATED : November 1, 1994
INVENTOR(S) : Naomi L. Nakao and John V. Mizzi It is certified that error appears in the above-indentified patent and that said Letters Patent is hereby corrected as shown below:

Column 4, line 17, change "comprising" to --comprises--.

Column 9, line 36, claim 16, change "input" to --inlet--.

Column 10, line 7, claim 21, change "18" to --20--.

Signed and Sealed this

Thirteenth Day of June, 1995

*Attest:*

BRUCE LEHMAN

*Attesting Officer*  *Commissioner of Patents and Trademarks*